(12) United States Patent
Yang et al.

(10) Patent No.: US 6,316,268 B1
(45) Date of Patent: *Nov. 13, 2001

(54) CHEMICAL MICROSENSORS FOR DETECTION OF EXPLOSIVES AND CHEMICAL WARFARE AGENTS

(75) Inventors: Xiaoguang Yang; Basil I. Swanson, both of Los Alamos, NM (US)

(73) Assignee: The Regents of the University of California, Los Alamos, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 09/308,460
(22) PCT Filed: Nov. 21, 1997
(86) PCT No.: PCT/US97/21519
  § 371 Date: May 17, 1999
  § 102(e) Date: May 17, 1999
(87) PCT Pub. No.: WO98/22795
  PCT Pub. Date: May 28, 1998

Related U.S. Application Data
(60) Provisional application No. 60/050,215, filed on Jun. 19, 1997, and provisional application No. 60/031,643, filed on Nov. 22, 1996.

(51) Int. Cl.[7] .................................................. G01N 33/22
(52) U.S. Cl. ........................... 436/106; 436/103; 436/104; 422/82
(58) Field of Search .................................... 436/103, 106, 436/104; 422/82

(56) References Cited

U.S. PATENT DOCUMENTS

| | | | |
|---|---|---|---|
| 4,860,573 | * 8/1989 | Barendz et al. | 73/23 |
| 5,151,110 | * 9/1992 | Bein et al. | 55/75 |
| 5,266,271 | * 11/1993 | Bankert et al. | 422/82.07 |
| 5,418,058 | * 5/1995 | Li et al. | 428/327 |

OTHER PUBLICATIONS

Chemical Abstracts 122:121994, 1994.*

* cited by examiner

Primary Examiner—Jill Warden
Assistant Examiner—Monique T. Cole
(74) Attorney, Agent, or Firm—Bruce H. Cottrell

(57) ABSTRACT

An article of manufacture is provided including a substrate having an oxide surface layer and a layer of a cyclodextrin derivative chemically bonded to said substrate, said layer of a cyclodextrin derivative adapted for the inclusion of selected compounds, e.g., nitro-containing organic compounds, therewith. Such an article can be a chemical microsensor capable of detecting a resultant mass change from inclusion of the nitro-containing organic compound.

9 Claims, 10 Drawing Sheets

US 6,316,268 B1

CHEMICAL MICROSENSORS FOR DETECTION OF EXPLOSIVES AND CHEMICAL WARFARE AGENTS

This application claims the benefit of U.S. Provisional Application No. 60/050,215 filed Jun. 19, 1997 and U. S. Provisional Application No. 60/031,643 filed Nov. 22, 1996.

FIELD OF THE INVENTION

The present invention relates to chemical microsensor devices including a layer of a cyclodextrin-derivative and to a process for the detection of trace amounts of selected organic compounds including nitro-containing organic compounds (e.g., explosives) and/or chemical warfare agents. This invention is the result of a contract with the Department of Energy (Contract No. W-7405-ENG-36).

BACKGROUND OF THE INVENTION

The detection of nitro-containing organic compounds is necessary for finding unexploded ordnance or buried land mines or for finding the presence of explosive materials, e.g., hidden within airline luggage. Safety or security concerns over such explosive materials require improved monitoring and/or, analysis for the detection of selected volatile nitro-containing compounds generally present as minor contaminants within common explosive compounds such as trinitrotoluene (TNT). While analytical techniques are available to detect the presence of many substances down to levels as low as parts per billion (ppb) or less, such analytical techniques generally require collecting a sample in the field, taking the sample to a laboratory, and analyzing the sample by, e.g., gas chromatography or mass spectroscopy. Such analysis requires sophisticated equipment that generally requires up to several days to obtain final results and such analysis is not generally suited to field use. Thus, present analytical techniques fail to provide any real-time information about the presence of nitro-containing organic compounds.

Another category of materials sought to be detected on a real-time basis are chemical compounds used in chemical warfare generally referred to as chemical warfare agents (CW agents) such as nerve gas or blister agents. The detection of CW agents to allow for protection of personnel or to allow for detection of suspected production sites is important.

Much prior research has been directed to developing chemical sensors that can give more rapid feedback information. One example is U.S. Pat. No. 5,151,110 wherein a sensor includes a piezoelectric substrate, preferably contained within a surface acoustic wave (SAW) device or a quartz crystal microbalance (QCM) device, and a coating, such as zeolite crystals in an inorganic silica matrix, applied to the substrate to selectively sorb chemical entities of a size less than a predetermined magnitude. While such a chemical sensor is useful, it is limited to materials that physically fit within the particular pore sizes of the zeolite crystals.

U.S. Pat. No. 4,860,573 describes a composite substrate intended for an apparatus for quantitative detection of, e.g., an organic component present in a gas or liquid. Cyclodextrin is described as one material for incorporation as an active site material into the composite substrate. However, there is no teaching or suggestion of multilayers of the active site material, nor is there any teaching or suggestion of using cyclodextrin derivatives or of forming oriented cyclodextrin derivative structures by the controlled assembly of such materials through layer by layer build up or addition.

U.S. Pat. No. 5,418,058, issued to Li et al. on May 23, 1995, describes chemical microsensors for the detection of selected organic compounds such as aromatic compounds, polyaromatic compounds, oxygen-containing organic compounds, and halogenated hydrocarbons. In the formation of the microsensor, a linking molecule of, e.g., bistrichlorosilylhexane, was used to covalently bond the sensing molecule, i.e., the cyclodextrin derivative, to the transducer surface. There is no teaching or suggestion of the detection or nitro-containing organic compounds with the disclosed chemical microsensors, nor any teaching or suggestion of asymmetrical linking agents for covalently bonding the cyclodextrin material to the transducer surface.

It is an object of the present invention to provide a chemical sensor including a cyclodextrin derivative and a method of detecting nitro-containing organic compounds and/or CW agents, preferably in an on-site, real time process.

It is a further object of the invention to provide a chemical microsensor, including a cyclodextrin derivative, having sensitivity to detect low levels of such nitro-containing chemical compounds or CW agents, preferably at a sub-ppb level.

It is a still further object of the invention to provide a reversible chemical microsensor including a cyclodextrin derivative.

Yet another object of the present invention is to provide a chemical microsensor formed through a layer by layer build up process.

Another object of the present invention is to provide a chemical microsensor formed through a layer by layer build up process using an asymmetrical bifunctional linking agent as one layer of the microsensor.

Still another object of the present invention is a chemical microsensor system utilizing a reference sensor substantially identical to a cyclodextrin-derivative containing sensor except for the cyclodextrin-derivative material layer.

Yet another object of the present invention is to form a chemical bond, i.e., a hydrogen bond between the cyclodextrin material and the target compounds.

Yet a further object of the present invention is to provide asymmetrical functionalization on the top rim of a cyclodextrin, e.g., some hydroxyl functionalization plus some methoxy functionalization, leaving at least one functionality with hydrogen bonding potential.

SUMMARY OF THE INVENTION

To achieve the foregoing and other objects, and in accordance with the purposes of the present invention, as embodied and broadly described herein, the present invention provides a chemical microsensor including a substrate including an oxide layer, a linking agent including a linear alkane chain containing from about 8 to about 18 carbon atoms attached to the oxide layer, and, a cyclodextrin-derivative covalently bonded to the linking agent.

The present invention further provides a method of detecting trace amounts of nitro-containing organic species within an environment including placing a selective chemical sensor into an environment, the sensor including a substrate having an oxide surface layer thereon and a selective thin film of a cyclodextrin derivative chemically bound upon the substrate, the film adapted for the chemically bonding of a nitro-containing organic compound therewith, for a sufficient time wherein nitro-containing organic species can form complexes with the cyclodextrin derivative, measuring a change resulting from complexation of nitro-containing chemical species with the cyclodextrin derivative, and correlating the measured change with a quantitative or qualitative output relating to the nitro-containing organic species.

In one embodiment of the invention is provided a chemical microsensor system including a first sensing portion including a first substrate having a surface oxide layer thereon, a linking agent including a linear alkane chain containing from about 8 to about 18 carbon atoms attached to the surface oxide layer of the first substrate, a cyclodextrin-derivative covalently bonded to the lining agent of first substrate, a second sensing portion including a second substrate having a surface oxide layer thereon, the linking agent including a linear alkane chain containing from about 8 to about 18 carbon atoms attached to the surface oxide layer of the second substrate, the first and second sensing portions electronically linked so as to provide measurements of a system wherein the second sensing portion serves as a reference to the first sensing portion.

DETAILED DESCRIPTION

Figure 1:
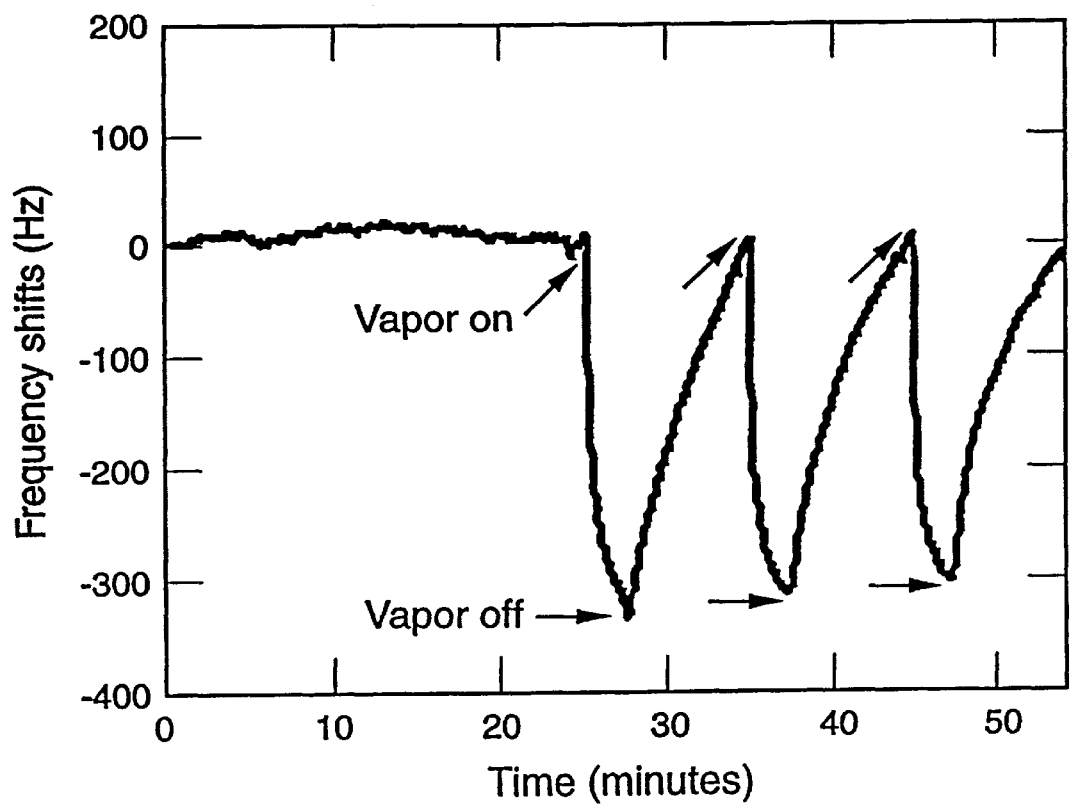
FIG. 1 illustrates the response of a 250 MHz SAW resonator microsensor coated with a β-cyclodextrin derivative in accordance with the present invention to a selected CW agent simulant.

The present invention is concerned with an article of manufacture, e.g., a chemical microsensor device including a substrate with a layer of a cyclodextrin derivative thereon, such a chemical microsensor device useful, e.g., for detecting nitro-containing organic compounds or CW agents. The chemical microsensor of the present invention is characterized as having both selectivity and sensitivity for nitro-containing organic compounds or CW agents, especially for nitro-containing organic compounds.

By "selectivity" is meant that the chemical microsensor demonstrates high response for the selected target material such as a nitro-containing organic compound while demonstrating either no response or a low response to other materials within a given sample. By "sensitivity" is meant that the chemical microsensor demonstrates high response for the selected target material at low concentrations, e.g., at concentration levels of less than about 100 ppb, preferably of less than about 10 ppb and more preferably at concentration levels as low as less than 1 ppb.

In contrast to previous cyclodextrin-derivative based chemical microsensors used to detect chlorinated hydrocarbons and chlorinated aromatics, the chemical microsensor of the present invention shows responses to nitro-containing organic compounds such as nitrobenzene of 2 to 3 orders of magnitude higher response in frequency shift thus greater sensitivity than for the previous chlorinated compounds and other volatile organic compounds.

The layer of cyclodextrin derivative upon the substrate is species selective, i.e., the layer of cyclodextrin derivative is selective for certain species within an admire based on a size basis wherein certain species have a size capable of fitting within the defined cyclodextrin cavity (the selective host material) and/or on a chemical basis wherein certain species can form a chemical attraction with a functionality upon the cyclodextrin derivative material. Where the cyclodextrin material is functioning as a selective host material, it should have a suitable opening or cavity whereby capture or inclusion of target selective organic compounds can occur. Additionally, the cyclodextrin material preferably includes a functionality capable of forming chemical binding, e.g., hydrogen bonding, with nitro-containing organic compounds. The present sensor mimics in some respects the behavior of an enzyme that has both geometric or structural requirements and chemical requirements for operation. Among the functionalities capable of forming chemical binding with nitro-containing organic compounds can be included hydroxyl (—OH), amino (—$NH_2$), phosphine (—$PH_2$) and —SH. The functionality can also be a substituted amino (—$NR_2$) where R can be an alkyl group such as a $C_1$ to $C_6$ alkyl group, or an N-containing heterocyclic such as pyridine or imidazole or may be ethylene diamine.

There may also be metal complexes attached to the cyclodextrin material such as lanthanide complexes for enhanced chemical binding or bonding with CW agents.

The layer of cyclodextrin derivative can generally consist of a single thin layer, e.g., a single monolayer, of the cyclodextrin-derivative material or can include multiple layers of the cyclodextrin-derivative material. Multiple layers may in some instances be preferred to enhance sensitivity of the cyclodextrin derivative material by providing additional inclusion sites and/or binding sites. In multiple layers, additional thin layer of the cyclodextrin-derivative material can be chemically bound upon bonding sites in each prior layer of the cyclodextrin-derivative material. There is generally no limit to the number of layers that can be employed although usually the number of layers will be from about 1 to about 100. In other instances, thin layers of the cyclodextrin derivative material resulting from a single monolayer or only a few single layers to obtain a good signal. For example, with high frequency acoustic resonators or with optical waveguides, careful molecular control during assembly of the microsensor may be necessary. Such molecular control can result in a single monolayer of the cyclodextrin derivative material with good response to a target material. Thicker films of the cyclodextrin derivative material may either result in loss of any detectable signal or change the response time to too slow. Generally, individual monolayers are on the order of about 2 nanometers (nm) to about 2.5 nm in thickness. Multiple layers may total up to about 1 micron in thickness.

The present chemical microsensors including the cyclodextrin-derivative material are useful for detection of nitro-containing organic compounds such as, e.g., nitrobenzene (NB), dinitrobenzene (DNB), trinitrobenzene (TNB), hexanitrobenzene (HNB), nitrotoluene (NT), dinitrotoluene (DNT), and the like or detection of CW agents, decomposition products of CW agents, or precursor materials to CW agents. In some instances, the detected nitro-containing organic compound can serve as a signature compound for another particular explosive material, e.g., nitrotoluene, dinitrotoluene or trinitrobenzene can serve as a signature compound for trinitrotoluene (TNT) which has a low volatility. In other instances, simulants of a material desired to be detected (e.g., simulants of CW agents) are tested instead of the material itself for obvious safety reasons. Exemplary simulants for CW agents include chloroethyl ethyl sulfide as a simulant for mustard gas and dimethoxy methyl phosphate as a simulant for sarin (methylphosphonofluoride acid, isopropyl ester) nerve gas. Measurements of frequency responses in chemical microsensors, e.g., surface acoustic wave devices incorporating the cyclodextrin-derivative material, have shown responses to nitrobenzene of two to three orders of magnitude higher in frequency shift than similar chemical microsensors incorporating the same or other cyclodextrin-derivatives have shown for chlorinated hydrocarbons and aromatic organic compounds. Detection of nitro-containing organic compounds are capable at levels as low as 10 to 100 parts per billion (ppb) of the selected nitro-containing organic compound using a single monolayer. By use of only a single monolayer of selected cyclodextrin-derivative material even lower detection limits down to less than 1 part per billion may be achieved. Proper selection of the chemical modification of the cyclodextrin-derivative material may control the ultimate sensitivity. Use of multiple layers of the cyclodextrin-derivative material may also allow for greater sensitivity, i.e., lower detection limits. Measurements of these same target materials (a nitro-containing organic compound such as nitrobenzene, or nerve gas simulants and mustard gas simulants) against reference films prepared from self-assembled thin films of an alkane ($H_{39}C_{18}SiCl_3$) or a perfluorinated alkane ($CF_3(CF_2)_7CH_2CH_2SiCl_3$) on a SAW device show a negligible response.

Cyclodextrins are linked D-glucopyranose units with α-cyclodextrin, β-cyclodextrin, γ-cyclodextrin being composed of 6, 7, or 8 units, respectively, the units linked into a circular arrangement. Accordingly, the internal diameter of each of α-cyclodextrin, β-cyclodextrin, γ-cyclodextrin vanes from the others. α-cyclodextrin has a cavity size or internal diameter of about 4.7 to 5.2 Angstroms (A), β-cyclodextrin has an internal diameter of about 6.0 to 6.5 A, and γ-cyclodextrin has an internal diameter of about 7.5 to 8.5 A.

The term "cyclodextrin derivative" refers to a cyclodextrin modified to include another functional group. This can be accomplished by the addition of other functional groups, e.g., a cyclodextrin wherein a hydrogen atom of one or more primary or secondary hydroxyl groups therein has been substituted by, e.g., a carboxyl group, a carboxyl alkyl group, a carboxylaryl group, an alkyl group, e.g., either a lower alkyl such as a $C_1$ to $C_4$ group or a longer chain aliphatic containing from about 8 to about 22 carbons, a hydroxyalkyl group, and the like. A hydroxyl group can also be modified by conversion to an amino group. Modification of a cyclodextrin can alter the length and size of the internal cavity or alter the chemical compatibility or binding properties of the particular cyclodextrin derivative with a nitro-containing organic compound or with a CW agent. For enhanced detection of CW agents such as sarin, modification of the cyclodextrin may preferably include formation of a metal complex ion such as a lanthanide complex.

A synthetic scheme or self-assembly scheme useful in practicing the present invention can include the following. In a cyclodextrin derivative, a secondary hydroxyl group can be reacted to convert the hydroxyl group to an ester group (OR). R in such an ester group can be an alkyl group, preferably a $C_1$ to $C_4$ alkyl group or substituted $C_1$ to $C_4$ alkyl group, an aryl group, preferably a phenyl or substituted phenyl, or a sulfonic group and the like. R can also be a carbonyl group such as $R_1C(=O)$— with $R_1$ being, e.g., hydrogen, an alkyl group, preferably a $C_1$ to $C_4$ alkyl group or substituted $C_1$ to $C_4$ alkyl group, or an aryl group, preferably a phenyl or substituted phenyl. Suitable groups for R can include: carboxyl groups wherein $R_1$ is methyl, ethyl, propyl, butyl, hydroxyethyl, hydroxypropyl, benzyl, and the like; alkyl groups such as methyl, ethyl, propyl, butyl, hydroxyethyl, hydroxypropyl, benzyl, and the like; or, aryl groups such as phenyl and the like. The resultant derivative can be linked through a linker agent after the linker agent is initially reacted to the oxide surface of a substrate. Orientation of the cyclodextrin cavity can thus be accomplished. Reaction with potassium hydroxide and methanol can restore a secondary hydroxyl functionality and the steps can be repeated to build up a multilayer structure with oriented cyclodextrin functionality.

For example, monolayers of both asymmmetric α- and β-cyclodextrin benzoate derivatives can be successfully attached to an oxide surface through covalent bonds via a linker agent. Covalent bonding between the cyclodextrin-derivative material and the linker material and between the linker material and the substrate surface provides high stability to the resultant chemical microsensor. Surface properties of the cyclodextrin derivative such as relative hydrophilicity or hydrophobicity can be chemically tailored. Such tailoring of the properties can change the selectivity and/or strength of chemical binding of the cyclodextrin derivative to target nitro-containing organic compounds or CW agents.

Multilayers of the cyclodextrin derivative can be built up by attaching a linker gent to surface hydroxyl groups, whether original cyclodextrin hydroxyl groups or subsequently generated hydroxyl groups. The construction of such multilayered cyclodextrin derivatives can be in a fashion referred to as self assembly.

In addition to covalent bonding to the oxide surface, such a step by step supramolecular self assembly technique offers molecular level manipulation of the nanostructure of the resultant material, e.g., in the orientation of the cyclodextrin derivatives. As both the α- and β-cyclodextrin secondary hydroxyl groups can be blocked by reaction to form benzoate groups, the building blocks of the cyclodextrin derivatives can easily be assembled with a molecular orientation ensuring that the cyclodextrin "bucket" faces outward from the initial oxide surface of the substrate thereby enhancing the response time in the formation of the inclusion complexes. Other functionalities attached to the secondary hydroxyl groups of the cyclodextrin may control access to the "bucket" or cavity of the cyclodextrin.

Cyclodextrins are commercially available, e.g., from Sigma Chemical Co., St. Louis, Mo. and from Aldrich Chemical Co., Inc., Milwaukee, Wis.

The substrates in the presently described invention are generally materials such as quartz, silicon, zinc oxide, zirconium oxide, tin oxide, indium-tin oxide, titanium oxide and lithium niobate. The substrates can be a part within a device such as a SAW device, a Lamb wave device, or an optical transducer, e.g., a waveguide device such as a Mach-Zehnder interferometer. The substrate may also be in the form of, e.g., beads or the like for use as a separation media.

In the process of forming articles or devices including a substrate with an oxide surface layer and the layer of a cyclodextrin-derivative material, a linking agent is employed between the oxide surface layer of the substrate and the cyclodextrin-derivative material. Among useful linking agents can be included those of the formula $Br(CH_2)_xSi(OR)_3$ where x is an integer from about 6 to about 18, preferably an integer from about 12 to about 18, more preferably an integer from about 16 to about 18, and R is selected from among methyl, ethyl, propyl and the like or chlorine. Another class of suitable linking agents include the formula $Br(CH_2)_xOH$ where x is an integer from about 6 to about 18, preferably an integer from about 12 to about 18, more preferably an integer from about 16 to about 18. Yet another class of suitable linking agents include alkenylsilanes such as 5-hexenyltrichlorosilane, 7-octenyltrichlorosilane and the like.

The linking agent is reacted initially with the oxide surface layer of the substrate to form an intermediate product which is then subsequently reacted with the desired cyclodextrin-derivative material. Optionally, the linking agent may be intially reacted with the cyclodextrin-derivative material to form an intermediate product which may subsequently be reacted with the oxide surface layer of the substrate. After formation of the initial layer of cyclodextrin-derivative material upon the substrate, a subsequent layer of the cyclodextrin-derivative material can be linked through additional linking agents linked to, e.g., a hydroxyl functionality of the first cyclodextrin-derivative material layer. Alternatively, a subsequent layer of the cyclodextrin-derivative material can be linked directly to, e.g., a hydroxyl functionality of the first cyclodextrin-derivative material layer.

The sensor devices of the present invention can be acoustic wave devices or optical transducers. Typically, acoustic wave devices are an arrangement of input and output interdigital transducers formed on a piezoelectric substrate such as quartz or lithium niobate. The input transducer, upon application of an alternating voltage, generates an alternating mechanical strain field because of the piezoelectric nature of the substrate. The alternating mechanical strain field launches an acoustic wave which if the wave travels along the substrate surface is called a surface acoustic wave (SAW) and if the wave travels through the bulk of the substrate is called an acoustic plate mode (APM). The acoustic wave interacts with a thin film formed on the device surface and is then reconverted into an electrical signal by the output transducer.

The velocity of the wave can be easily determined by operating the device as the feedback element of a oscillator circuit using an RF amplifier. Relative changes in frequency (f) can be directly related to relative changes in wave velocity (v). In situations where the velocity shift (Dv) is dominated by changes in the mass density of the film (m, mass/area), these frequency changes (Df) can be directly related to changes in mass density by:

$$Df/f_o = Dv/v_o = -c_m f_o m,$$

where $c_m$ is a mass sensitivity constant which depends on the piezoelectric substrate, and the subscript "o" indicates the unperturbed velocity or frequency.

Identification of species within a liquid or aqueous environment can be better achieved with an APM or Lamb wave device, which are each more effective in liquids than SAW devices which are highly attenuated by liquids contacting the device surface.

Lamb waves propagate through materials of finite thickness. In contrast to a surface acoustic wave, which requires a propagation medium having a thickness on the order of tens to hundreds of times the wavelength of the surface acoustic wave propagating therethrough, Lamb waves require a propagation medium which is at most only several wavelengths in thickness.

Lamb wave sensors generally operate in a frequency range of from about 1 MHz to about 200 MHz, while SAW sensors generally operate in frequency range of from about 10 MHz to about 2,000 MHz. The lower-frequency operation of Lamb wave sensors can be more convenient in terms of costs for associated electronic equipment such as frequency counters and feedback amplifiers. Lamb devices are well known and are described, e.g., in U.S. Pat. Nos. 5,212,988, 5,189,914 and 5,129,262.

Suitable optical transducer devices can be, e.g., a Mach-Zehnder interferometer wherein the cyclodextrin-derivative is attached to an oxide surface of one arm of a split waveguide. After formation of any inclusion complexes, a refractive index change would result. The change in refractive index would be measured by a phase shift comparison between the light in the two arms of the interferometer, one arm coated with the selective film and one arm uncoated, thus allowing for determination and detection of selected chemical species. Generally, use of an optical transducer may allow for a more sensitive detection limit than by use of an acoustic wave device such as a SAW device or a Lamb wave device. Moreover, the response of SAW type devices and optical waveguide devices will generally be different for particular chemical species thereby providing complementary information about the identity of the chemical species.

In operation, a surface acoustic wave is launched by applying a rf potential to the source transducers, e.g., source metal interdigital transducers.

Such a SAW resonator device sets up a resonating cavity in operation and such a SAW resonator device is available (without coating) from, e.g., MicroSensors Systems, Inc., as, e.g., an SAW-SR 200A (a 200 MHz on ST quartz). In operation, using both a coated and uncoated resonator device for comparison, a surface acoustic wave is launched by applying a rf potential to the source transducers of the respective resonators, e.g., source metal interdigital transducers. The wave transverses the surface of the piezoelectric quartz through the respective uncoated and coated resonators and the wave is then converted back to an electrical signal at the pick up transducers, e.g., pick up metal interdigital transducers. The respective electrical signals are passed through a mixer and a frequency shift is obtained. As the cyclodextrin coating changes in weight due to inclusion of or chemical binding to, e.g., nitro-containing organic compounds or CW agents, the frequency shift will change.

Formation of a chemical separator in the present invention involves securing a cyclodextrin derivative material onto a suitable substrate, e.g., a quartz substrate, having a oxide surface to facilitate chemical bonding through, e.g., a linking agent. The resultant device can function as a chemical separator for nitro-containing organic compounds by forming reversible complexes with selected nitro-containing organic compounds such as nitrobenzene and the like. After initial formation of the inclusion complex, reversal can be accomplished, e.g., by varying the temperature up to about 60° C. thereby yielding a separation of the particular nitro-containing organic compounds from the chemical separator.

Other potential applications of the chemical microsensors of the present invention include use in process monitoring for industrial chemicals, use in toxic organic compound monitoring of gas phases for safety, use in environmental monitoring of storage tank leaks, or use in monitoring of sensitive areas such as airports for restriction of terrorist activities.

The present invention is more particularly described in the following examples which are intended as illustrative only, since numerous modifications and variations will be apparent to those skilled in the art.

All reagents were purchased from commercial sources except for cyclodextrin-derivatives. All syntheses were carried out under an inert atmosphere. Examples A–N relate to the preparation of various cyclodextrin derivatives. NMR spectra were obtained on a Brucker 250 MHz spectrometer.

EXAMPLE A

Heptakis(2-O-methyl)-β-cyclodextrin was prepared as follows. β-cyclodextrin from Aldrich was purified by recrystallization from water and methanol and dried in vacuum. β-cyclodextrin (1 g, 0.88 mmol) was dissolved in 10 ml freshly distilled dimethyl sulfoxide (DMSO). Sodium hydride (60% dispersion in mineral oil, 0.246 g, 6.16 mmol) was added. The mixture was stirred at room temperature for about 7 hours. Methyl iodide (0.87 g, 0.38 ml) was added and the solution was stirred for 12 hours. The volatile materials were removed in vacuum and the oily residue was extracted with methanol to give 0.75 g of white solid, which was characterized by NMR and IR spectroscopy as the desired cyclodextrin.

EXAMPLE B

Preparation of heptakis(2-O-benzyl)-β-cyclodextrin was prepared as follows. β-cyclodextrin (1 g, 0.88 mmol) and sodium hydride (60% dispersion in mineral oil, 0.264 g, 6.16 mmol) were placed in a Schlenk flask and the flask was evacuated and filled with nitrogen three times. Freshly distilled DMSO (10 ml) was added and the mixture was stirred at room temperature at room temperature for 15 hours. The resulting sticky solution was treated with benzyl chloride (0.71 ml) and the solution was stirred for 24 hours. The solution was concentrated to about 10 ml. Acetone was then added to precipitate a solid. After filtration, the solid was extracted with methanol to give a white solid (yield: 0.72 g). The compound was characterized with NMR spectroscopy.

EXAMPLE C

Hexakis(2-O-methyl)-α-cyclodextrin was prepared as follows. All syntheses were carried out under an inert atmosphere. α-cyclodextrin from Aldrich was purified by recrystallization from water and methanol and dried in vacuum. α-cyclodextrin (1.1 g, 1.13 mmol) was dissolved in 40 ml freshly distilled DMSO. Sodium hydride (60% dispersion in mineral oil, 0.247 g, 6.79 mmol) was added. The mixture was stirred at room temperature for about 15 hours. Methyl iodide (0.96 g, 0.42 ml) was added and the solution was stirred for 24 hours. The volatile materials were removed in vacuum and the oily residue was extracted with methanol to give 0.60 g of white solid, which was characterized by NMR and IR spectroscopy as the desired cyclodextrin.

EXAMPLE D

Hexakis(2-O-benzyl)-α-cyclodextrin was prepared as follows. α-cyclodextrin (1 g, 0.97 mmol) and sodium hydride (60% dispersion in mineral oil, 0.247 g, 6.79 mmol) were placed in a Schlenk flask and the flask was evacuated and filled with nitrogen three times. Freshly distilled DMSO (40 ml) was added and the mixture was stirred at room temperature for 15 hours. The resulting sticky solution was treated with benzyl chloride (0.71 ml) and the solution was stirred for 24 hours. The solution was concentrated to about 10 ml. Acetone was then added to precipitate a solid. After filtration, the solid was extracted with methanol to give a white solid (yield: 0.65 g). The compound was characterized with NMR spectroscopy.

EXAMPLE E

Heptakis(2-O-amino)-β-cyclodextrin was prepared as follows. Hexakis(2-O-amino)-β-cyclodextrin may be prepared from heptakis(2-O-tosyl)-β-cyclodextrin and sodium azide in dirmethylformaride (DMF). The resulting heptakis(2-O-azido)-β-cyclodextrin could be reduced to hexakis(2-O-amino)-β-cyclodextrin.

EXAMPLE F

Hexakis(2-O-amino)-α-cyclodextrin was prepared as follows. Hexakis(2-O-amino)-α-cyclodextrin may be prepared from hexakis(2-O-tosyl)-α-cyclodextrin and sodium azide in DMF. The resulting hexakis(2-O-azido)-α-cyclodextrin could be reduced to hexakis(2-O-amino)-α-cyclodextrin.

EXAMPLE G

Heptakis(2,3-di-O-methyl)-β-cyclodextrin was prepared as follows. All syntheses were carried out under an inert atmosphere. Heptakis(6-O-tert-butyldimethylsilyl)-β-cyclodextrin (0.37 g, 0.20 mmol) and sodium hydride (60% dispersion in mineral oil, 0.2 g) were dissolved in 15 ml freshly distilled DMF. The mixture was stirred at room temperature for about 2 hours. Methyl iodide (2 ml) was added and the solution was stirred for 15 hours. The reaction was quenched with 20 ml $H_2O$ and 20 ml methylene chloride. The organic phase was separated and dried over $MgSO_4$ to give an oily residue. This residue was then dissolved in tetrahydrofuran (THF) and treated with an 1M THF solution of t-$Bu_4NF$ (2 ml). After two hours, THF was removed in vacuum and the residue was treated with methylene chloride and water. The organic phase was separated and dried over $MgSO_4$ to give 100 milligrams (mg) of white solid. This material allows determination of the effectiveness of such cyclodextrin materials without the hydrogen bonding potential from the hydroxyl groups.

EXAMPLE H

Heptakis(2,3-di-O-benzyl)-β-cyclodextrin was prepared as follows. Heptakis(6-O-tert-butyldimethylsilyl)-β- cyclodextrin (0.37 g, 0.20 mmol) and sodium hydride (60% dispersion in mineral oil, 0.2 g) were dissolved in 15 ml freshly distilled DMF. The mixture was stirred at room temperature for about 2 hours. Benzyl chloride (0.28 g, 2.2 mmol) was added and the solution was stirred for 15 hours. The reaction was quenched with 20 ml water and 20 ml methylene chloride. The organic phase was separated and dried over $MgSO_4$ to give white solid (220 mg). This solid was then dissolved in THF and treated with an 1M THF solution of $tBu_4NF$ (2 ml). After two hours, THF was removed in vacuum and the residue was treated with $CH_2Cl_2$ and $H_2O$. The organic phase was separated and dried over $MgSO_4$ to give 150 mg white solid.

EXAMPLE I

Preparation of β-cyclodextrin lanthanide complexes is as follows. Mono(2-O-ethylenediamine)-β-cyclodextrin lanthanide complexes may be synthesized as follows: β-cyclodextrin (1 g, 0.88 mmol) is dissolved in 10 ml freshly distilled DMSO. Sodium hydride (60% dispersion in mineral oil, 0.246 g, 6.16 mmol) was added. The mixture is stirred at room temperature for about 7 hours. Tosyl chloride (1 mmol) is added and the solution is stirred for 12 hours. The volatile materials are removed in vacuum and the oily residue is extracted with methylene chloride to give mono (2-O-tosyl)-β-cyclodextrin. Mono(2-O-tosyl)-β-cyclodextrin (0.5 mmol) is dissolved in 10 ml DMF and treated with ethylenediamine (2 mmol) in DMF. The resulting mono(2-O-ethylenediamine)-β-cyclodextrin (0.2 mmol) is treated with 3 equivalent of $Ln(NO_3)_x$ in $H_2O$ to give the desired product.

EXAMPLE J

Preparation of tetra(O-hydroxyethyl)-t-butyl-calix[4] arene was as follows. Tetra(O-ethyl acetate)-t-butyl-calix[4] arene (3 g, 3 mmol) was dissolved in 20 ml freshly distilled THF. LiBH in THF (2M, 9 ml) was added, followed by dropwise addition of methanol (0.8 ml). The solution was refluxed for 2 hours and was treated with aqueous HCl solution (0.1 M). The organic phase was extracted with methylene chloride and dried over $MgSO_4$ with a yield of 2.3 grams. $^1HNMR$ ($CDCl_3$): 6.85, 4.36, 3.23, 4.00, 3.99. 1.09 ppm.

EXAMPLE K

Heptakis(6-O-8-octene-1-enyl)-β-cyclodextrin was prepared as follows. 1 g of dried β-cyclodextrin was dissolved in 25 ml of anhydrous dimethyl sulfoxide. To the solution was added 0.25 g of powdered sodium hydroxide and the mixture was stirred for one hour at room temperature. To the stirred solution, was added 1.03 ml of 8-Bromo-1-octene dropwise. Stirring was continued for 48 hours at room temperature. Sodium bromide and unreacted sodium hydroxide were separated from the reaction mixture by filtration and the solvent was removed subsequently under vacuum. The residue was dissolved in 10 ml methanol and the product was precipitated by adding 100 ml of diethyl ether. The crystalline product was separated by suction filtration and was dned under vacuum.

EXAMPLE L

Heptakis(2,3-O-dimethyl-6-O-8-octene-1-enyl)-β-cyclodextrin was prepared as follows. Heptakis(6-O-8-octene-1-enyl)-β-cyclodextrin (0.5 g) was dissolved in 25 ml of anhydrous dimethyl formamide. Sodium hydride (0.15 g) was added under a nitrogen atmosphere. The mixture was stirred for 2 hours at room temperature. Methyl iodide (0.123 ml) was added slowly at 20° C. After stirring for 30 minutes, another 0.123 ml of $CH_3I$ was added to the reaction mixture. After stirring for one hour the reaction mixture was decanted from unreacted sodium hydride and was carefully poured into 200 ml of water. The aqueous phase was extracted three times with 70 ml of chloroform. The combined organic portions were washed three times with water and dried over anhydrous $MgSO_4$. The crude product was purified by gel chromatography on Sephadex resin.

EXAMPLE M

A cyclodextrin-siloxane polymer was prepared via hydrosilylation as follows. Poly(methylhydrosiloxane) (20 μl) from Aldrich Chemical Co. was dissolved in 20 ml of dried toluene. 30 μl of 1-hexene was added to the solution and to the refluxing mixture a few drops of $H_2PtCl_6$ in anhydrous tetrahydrofuran was added at intervals of 2.5 hours each. After 24 hours, heptakis(2,3-O-dimethyl-6-O-8-octene-1-enyl)-β-cyclodextrin (0.2 g) was added to the mixture and the solution was stirred for another 24 hours. The solvent was removed and the resultant product was extracted by petroleum ether and dried under vacuum.

EXAMPLE N

Another cyclodextrin-siloxane polymer was prepared via hydrosilylation as follows. Poly(methylhydrosiloxane) (20 μl) from Aldrich Chemical Co. was dissolved in 20 ml of dried toluene. Heptakis(2,3-O-dimethyl-6-O-8-octene-1-enyl)-β-cyclodextrin (0.15 g) was added to the solution, followed with the addition of a few drops of $H_2PtCl_6$ in anhydrous tetrahydrofuran at intervals of 2.5 hours each. The solution was refluxed overnight.

EXAMPLE 1

Monolayer formation of heptakis(2-O-Methyl)-β-cyclodextrin on a SAW transducer with a siloxane linker was as follows. A surface acoustic wave (SAW) device was rinsed with acetone and chloroform and cleaned in a plasma cleaner for 10 mm. The device was then immersed in a toluene solution of bromoundecyltrimethoxysilane (2% v/v in toluene) for 24 hours under nitrogen. The device was then rinsed thoroughly with toluene and chloroform. The device was then immersed into a N-methyl-pyrrolidinone solution (10 ml) containing KOCN (22 mg) and heptakis(2-O-methyl)-β-cyclodextrin (24 mg). The solution was heated at 75° C. for 15 hours. The SAW device was rinsed with chloroform.

EXAMPLE 2

Monolayer formation of hexalds(2-O-benzyl)-α-cyclodextrin on a SAW transducer with an ether linker was as follows. A surface acoustic wave (SAW) device was rinsed with acetone and chloroform and cleaned in a plasma cleaner for 10 minutes. The device was then immersed in a neat 12-bromododecanol at 100° C. for 24 hours under nitrogen. The device was then rinsed thoroughly with chloroform. The device was then immersed into a N-methyl-pyrrolidinone solution (10 ml) containing KOCN (22 mg) and heptakis(2-O-benzyl)-α-cyclodextrin (24 mg). The solution was heated at 75° C. for 15 hours. The SAW device was rinsed with chloroform.

EXAMPLE 3

Monolayer formation of long alkyl chains on a SAW transducer was as follows. Three different SAMs (self assembled monolayers) were formed to passivate the surface of SAW devices. Long alkyl chain compounds of octadecanol, octadecyltrinethoxylsilane and heptadecafluoro-1,1,2,2-tetrahydrodecyltriethoxysilane were used to form the self assembled monolayers through either siloxane or ether linkages. A typical procedure was as follows: octadecyltrimethoxylsilane (0.2 ml) was dissolved in 10 ml toluene and a freshly cleaned SAW device (rinsed with chloroform and plasma cleaned for 10 minutes) was immersed in the solution. After one day, the SAW device was cleaned first with chloroform, then with acetone and then air-dried. An octadecanol monolayer was prepared by immersing a freshly cleaned SAW device into a neat octadecanol solution at 100° C. for 3 days. The device was washed with chloroform and ethanol.

Figure 5:
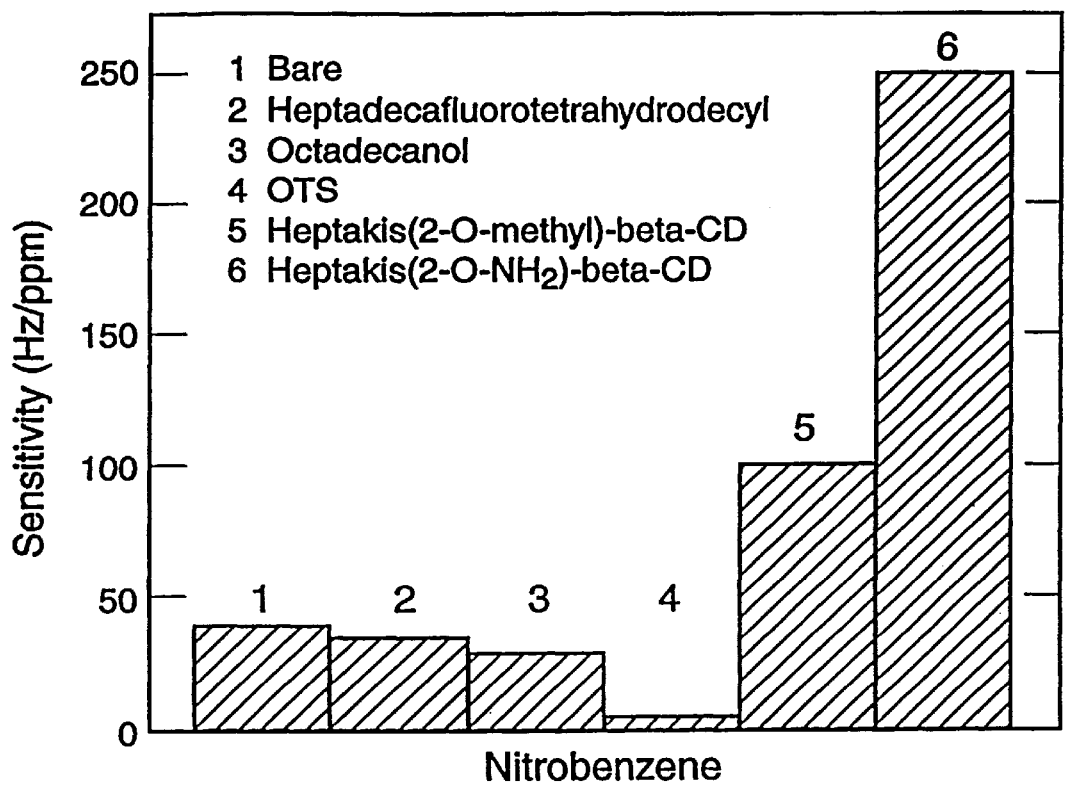
FIG. 5 illustrates the response of a 250 MHz SAW resonator microsensor coated with various materials in accordance with the present invention to nitrobenzene and demonstrates the passivation of the surface with a coating of octadecyltrichlorosilane.

The bar chart of FIG. 5 shows the results of various SAW measurements. The results indicate that the octadecyltrichlorosilane film coated SAW device is less sensitive to nitrobenzene than those SAW devices coated with a film of heptadecafluorotetrahydrodecyl, octadecanol, heptakis(2-O-methyl)-beta-cyclodextrin, or heptakis(2-O-amino)-beta-cyclodextrin. Such a passivated surface can serve as a good comparison for other measurements.

EXAMPLE 4

Monolayer formation of tetra-(O-hydroxyethyl)-t-butyl-calix[4]arene on a SAW transducer was as follows. A surface acoustic wave (SAW) device was rinsed with acetone and chloroform and cleaned in a plasma cleaner for 10 minutes. The device was then immersed in a toluene solution of bromoundecyltrimethoxysilane (2% v/v in toluene) for 24 hours under nitrogen. The device was then rinsed thoroughly with toluene and chloroform. The device was then immersed into a N-methyl-pyrrolidinone solution (10 ml) containing KOCN (22 mg) and tetra-(ethyl-O-acetate)-t-butyl-calix[4]arene (24 mg). The solution was heated at 75° C. for 15 hours. The SAW device was rinsed with chloroform.

EXAMPLE 5

Formation of a cyclodextrin-containing polymer thin film on a SAW transducer was as follows. A 250 Hz SAW device was cleaned by rinsing with acetone and irradiated with an $O_3$/UV cleaner. The freshly cleaned device was placed in a toluene solution containing the cyclodextrin-siloxane polymer (9 millimoles) of example M. The SAW device was then slowly pulled out of the solution and the device was placed under a strong nitrogen stream. The mass loading resulted in a frequency shift of about 500 KHz.

EXAMPLE 6

Fabrication of a covalent bonded cyclodextrin-siloxane polymer thin film on a SAW device was as follows. The process consisted of two steps. First, a SAW device was rinsed with acetone and cleaned with an $O_3$/UV. The device was then immersed in a solution including 3 millimoles of 5-hexenyltrichlorosilane in bicyclohexyl/carbon tetrachloride (9:1; volume to volume(v:v)) for one hour. The device was rinsed extensively with chloroform and dried in air. The cyclodextrin-siloxane polymer was prepared from poly (dimethylsiloxane) which contained about 30% Si—H groups (20 μl) and heptakis(2,3-O-dimethyl-6-O-8-octene-1-enyl)-β-cyclodextrin (0.2 g) in 20 mL toluene. The reaction took 24 hours with the addition of a few drops of the catalyst $H_2PtCl_6$ in anhydrous tetrahydrofiran added at 2.5 hour intervals. The SAW device was then placed in the solution. The solution was kept at 110° C. for another 24 hours. The SAW device was washed thoroughly with toluene and sonicated in toluene. The mass-loading resulted in a frequency shift of about 100 KHz.

EXAMPLE 7

Fabrication of a covalent bonded cyclodextrin-siloxane polymer thin film on a SAW device was as follows. The process consisted of two steps. First, a SAW device was rinsed with acetone and cleaned with an $O_3$/UV. The device was then immersed in a solution including 3millimoles of 5-hexenyltrichlorosilane in bicyclohexyl/carbon tetrachloride (9:1; v:v) for one hour. The device was rinsed extensively with chloroform and dried in air. The device was then immersed in the above prepared polymethylhydrosiloxane-cyclodextrin solution of example N. The solution was refluxed for 24 hours with the addition of a few drops of the catalyst $H_2PtCl_6$ in anhydrous tetrahydrofuran at 2.5 hour intervals. The SAW device was then placed in the solution. The solution was kept at 110° C. for another 24 hours. The SAW device was washed thoroughly with toluene and sonicated in toluene. The mass-loading resulted in a frequency shift of about 100 KHz.

Figure 10:
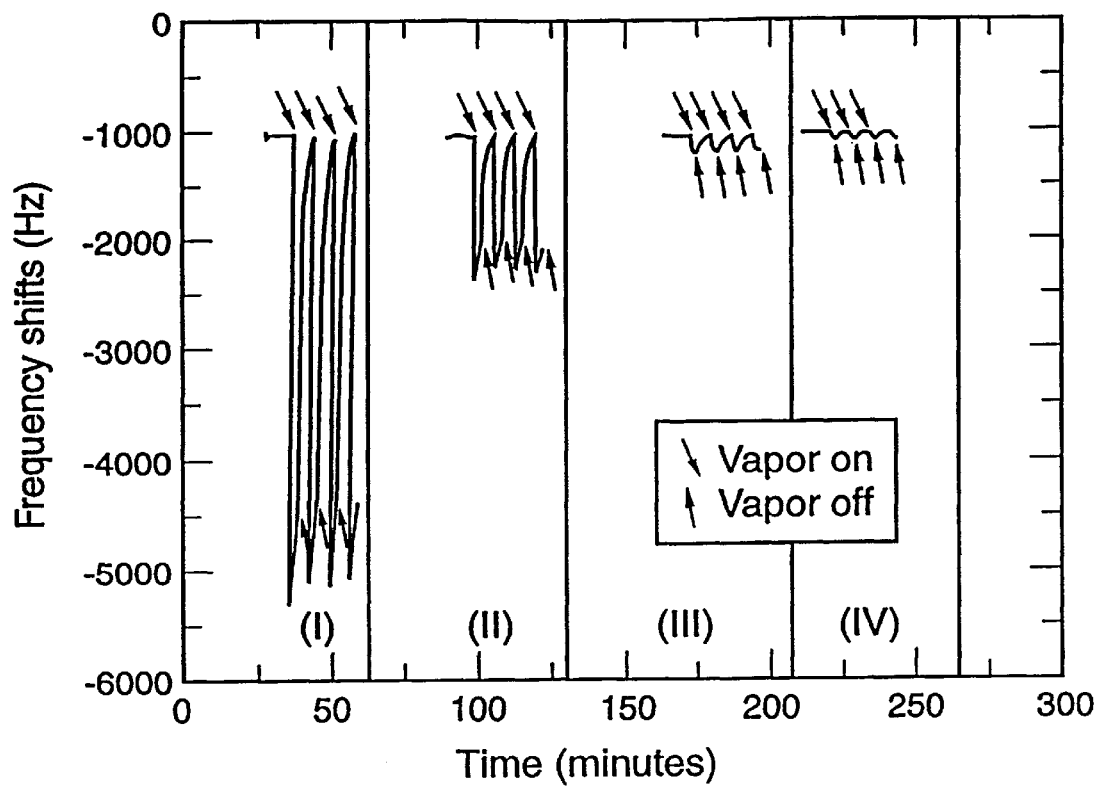
FIG. 10 shows the real time SAW response towards o-nitrotoluene vapor over a 250 MHz SAW device coated with cyclodextrin-polymethylhydrosiloxane polymer at o-nitrotoluene concentrations of (I) 6 ppm, (II) 600 ppb, (III) 60 ppb and (IV) 6 ppb.

The above SAW device was exposed to o-nitrotoluene (NT), a TNT surrogate. The device was found to detect o-nitrotoluene as low as 600 ppt with a response of 10 Hz. In FIG. 10, a real time response of the device to o-nitrotoluene at several concentrations is shown.

EXAMPLE 8

Detection of Simulants of Explosives and CW Agents

SAW Measurements

Two CW agent simulants were tested with the self assembled monolayer SAW sensors. DMMP has been widely used as nerve agents simulant for decontamination and sensor studies. Chloroethyl ethyl sulfide (CEES) has also been used as mustard gas simulant for decon study. In FIG. 1, a real time response of a heptakis(2-O-methyl)-β-cyclodextrin (from example 1) monolayer SAW device towards 23 ppm chloroethyl ethyl sulfide is shown. It can be seen that adsorption of CEES took a while to saturate the monolayer film and to desorb from the surface, which resulted in a peak-like response. Similar response peaks were observed for polymer coated SAW devices for organophosphorus compounds. The SAW sensitivity at 23 ppm CEES concentration is 15 Hz/ppm. With the same device, a response of 27 Hz was observed towards 2.3 ppm CEES. Also tested was a SAW device coated with octadecanol SAM (example 3) for sensing CEES, but no SAW response was observed at 23 ppm CEES.

Figure 2:
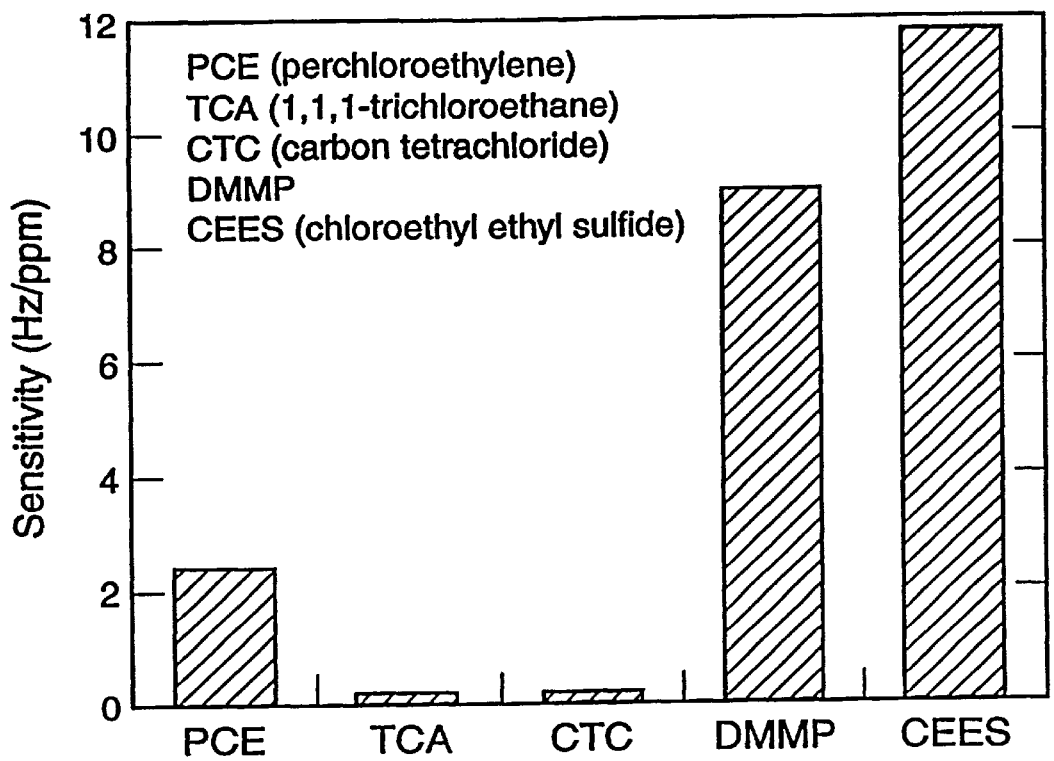
FIG. 2 illustrates a comparision of sensitivities of a cyclodextrin monolayer SAW device for detecting CW agent simulants and halogenated hydrocarbons.

FIG. 2 shows a comparison of sensitivities of a cyclodextrin monolayer SAW device for detecting CW agent simulants and halogenated hydrocarbons. It can be seen that the sensor coated as in example 1 was very sensitive towards CW agents simulants. The strong affinity of the cyclodextrin hosts toward DMMP and CEES can be attributed to the higher sensitivity.

Figure 3:
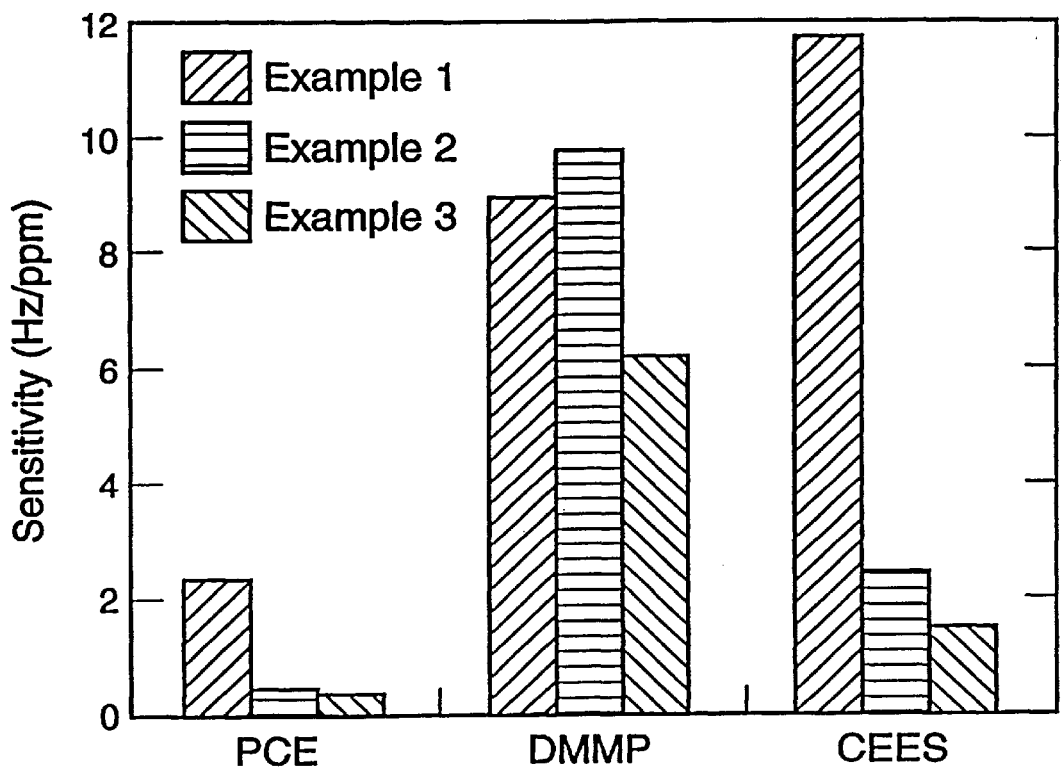
FIG. 3 illustrates sensor responses of three different monolayer SAW devices toward perchloroethylene, dimethoxy methyl phosphonate, and chlorethyl ethyl sulfide.

In FIG. 3, sensor responses of three different monolayer SAW devices (coated as in examples 1, 2 and 3) toward perchloroethylene, dimethoxy methyl phosphonate, and chlorethyl ethyl sulfide are presented. In the graph, the leftmost bar is for a SAW device with the coating as in example 1, the center bar is for a SAW device with the coating as in example 2 and the rightmost bar is for a SAW device with the coating as in example 3. These devices are quite sensitive toward DMMP with example 2 showing as the most sensitive. It was considered a surprise that the device with $C_{18}H_{33}$ monolayer (from example 3) had such a response toward DMMP. While not wishing to be bound by the present explanation, it is believed that some organic species are capable of intercalating between such long alkyl chains. In the case of CEES, however, the SAW device with methylated β-CD (from example 1) is extremely sensitive and the detection limit, as mentioned before, is 2.3 ppm.

Figure 4:
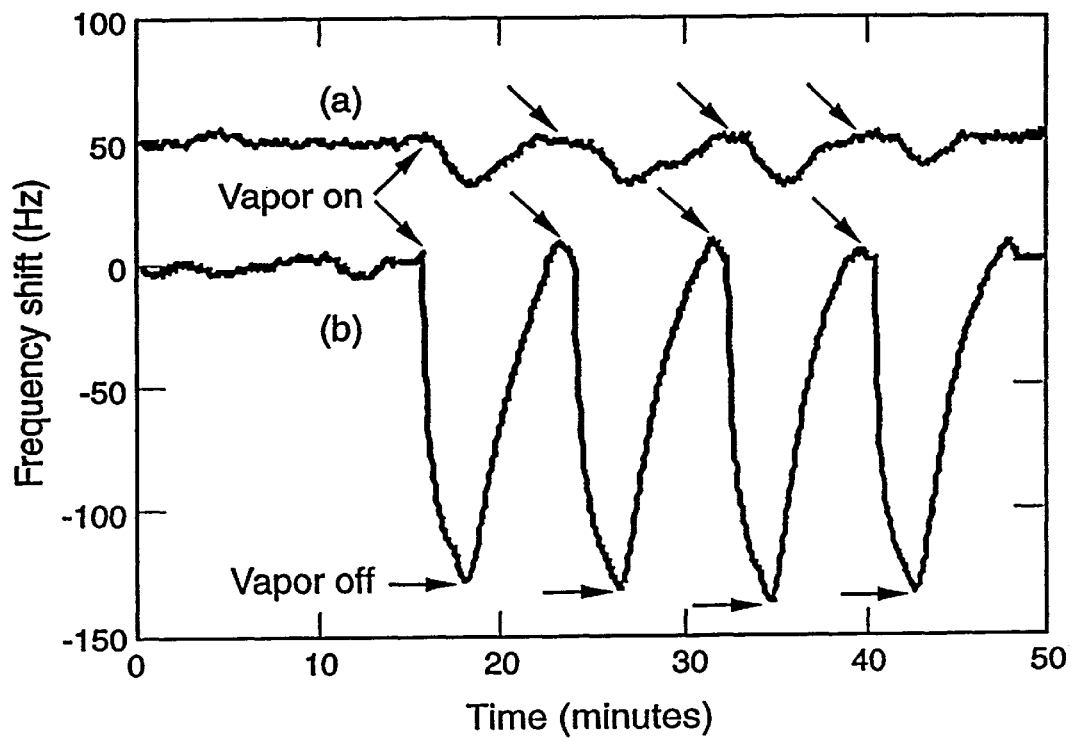
FIG. 4 illustrates the response of a 250 MHz SAW resonator microsensor coated with a cyclodextrin derivative in accordance with the present invention to nitrobenzene.

FIG. 4 shows a real-time response of a SAW sensor (from example 1) to (A) 150 ppb nitrobenzene in Argon with sensitivity of about 100 Hz/ppm and (B) 1.5 ppm nitrobenzene in Argon with sensitivity of about 97 Hz/ppm.

The sensing ability of the above fabricated devices were measured on explosive simulant (nitrobenzene) and CW agent simulants (dimethoxy methyl phosphonate and chloroethyl ethyl sulfide). Vapors of these simulants were generated and/or diluted to a certain concentration with a vapor generator. The sensitivity and detection limits of the chemical sensors are tabulated below.

TABLE 1

|  | Nitrobenzene | DMMP | Chloroethyl Ethyl Sulfide |
| --- | --- | --- | --- |
| Example 1 | 100 Hz/ppm | 8 Hz/ppm | 12 Hz/ppm |
| Example 2 | 20 Hz/ppm | 10 Hz/ppm | 5 Hz/ppm |

The above results demonstrate that upon exposure to the nitro-containing organic compound the cyclodextrin derivative coated SAW resonators of this invention responded both quickly (a matter of seconds) and reversibly as shown, e.g., in FIG. 4. Further, the results demonstrate that a chemical sensor including an active responsive material of a cyclodextrin derivative can detect the presence of volatile organic species in a real time situation and that such the active responsive material of such a sensor operates reversibly.

Figure 6:
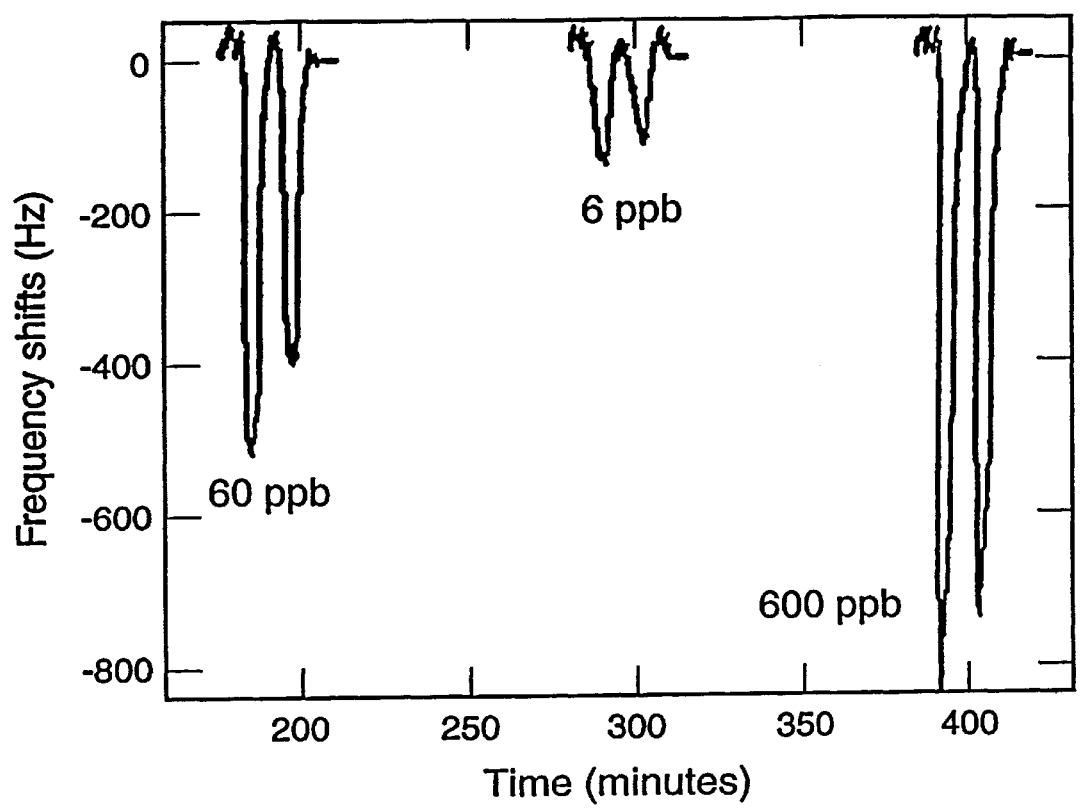
FIG. 6 illustrates the response of a SAW resonator microsensor coated with a cyclodextrin-siloxane polymer in accordance with the present invention to nitrobenzene.
Figure 7:
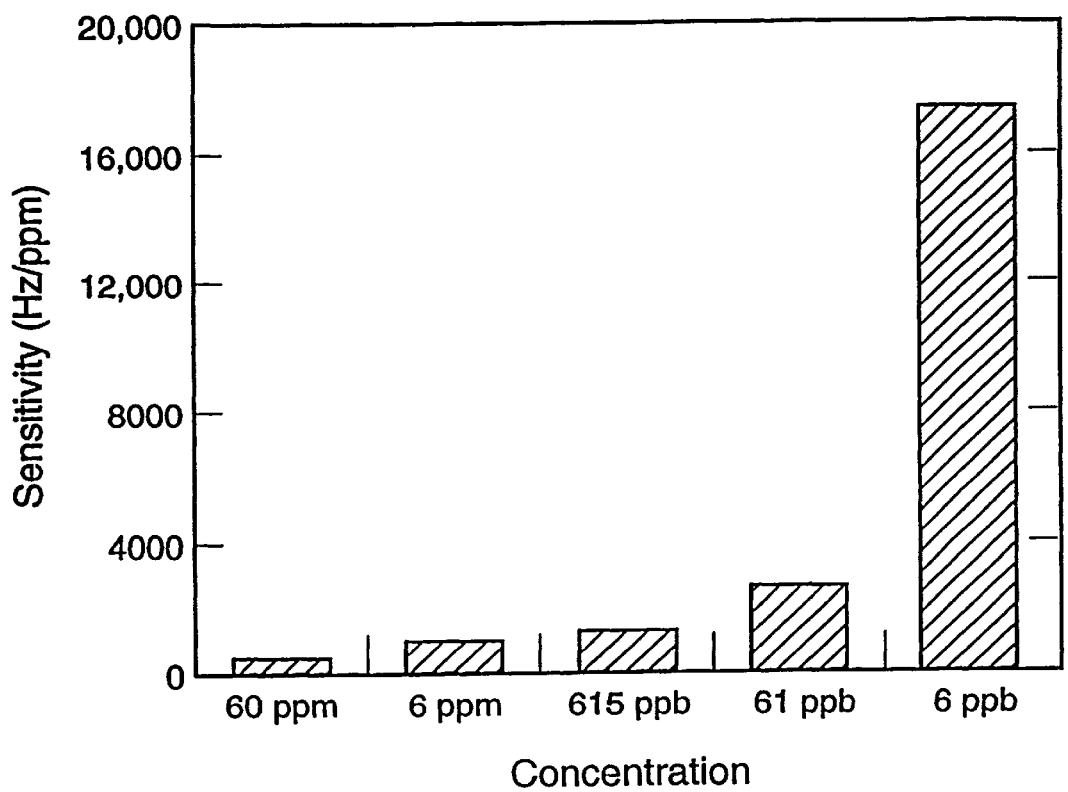
FIG. 7 illustrates the nonlinear response of a SAW resonator microsensor coated with a cyclodextrin-siloxane polymer in accordance with the present invention to nitrobenzene.
Figure 8:
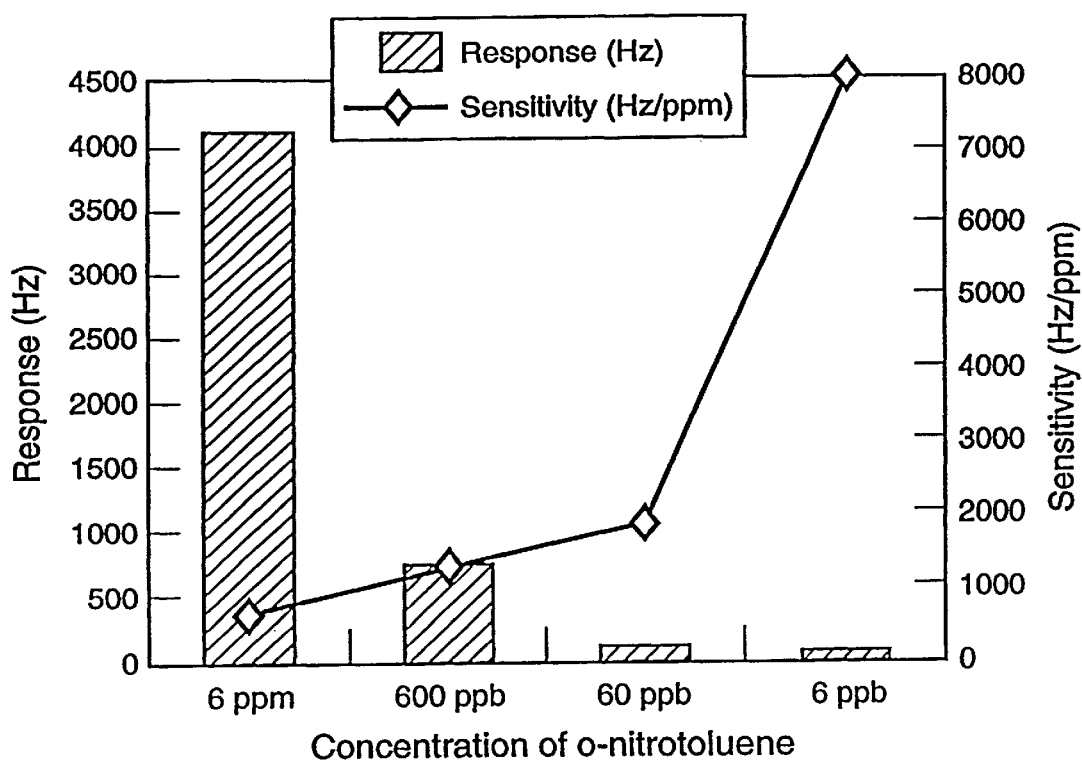
FIG. 8 illustrates the response of a SAW resonator microsensor coated with a second cyclodextrin-siloxane polymer in accordance with the present invention to o-nitrotoluene.

The self assembled SAW sensor of example 5 was tested for sensing nitrobenzene and the results are shown in FIG. 6. The response to the nitrobenzene was found to be nonlinear, i.e., at low concentrations the SAW device was much more sensitive. This result is shown in FIG. 7. The self assembled SAW sensor of example 7 was tested for sensing o-nitrotoluene and the results are shown in FIG. 8.

Figure 9:
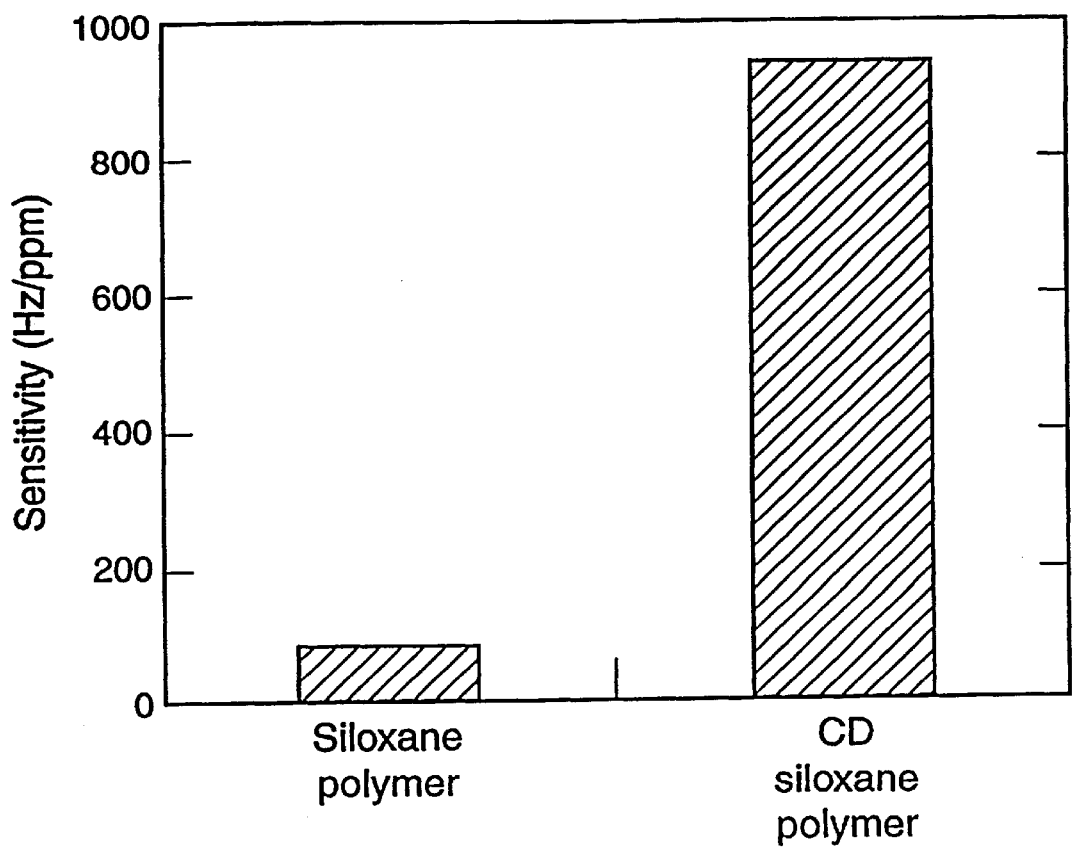
FIG. 9 illustrates the comparative response of a SAW resonator microsensor coated with a siloxane polymer versus of a SAW resonator microsensor coated with a cyclodextrin-siloxane polymer in accordance with the present invention to nitrobenzene.

For comparison, a SAW device was coated with only a siloxane polymer and compared to the SAW device of example 5. The sensitivity was found to be much lower for the device coated only with the siloxane as seen in the results plotted in FIG. 9. The siloxane polymer coated SAW device was found to have a detection limit of 6 ppm of nitrobenzene.

EXAMPLE 9

Fabrication of a cyclodextrin-polysiloxane film was as follows. A SAW device was reinsed with acetone and cleaned with an $O_3$/UV cleaner. The device was then immersed in a solution including 3 millimoles of 5-hexenyltrichlorosilane (in one run) or 7-octenyltrichlorosilane (in another run) in bicyclohexyl/carbon tetrachloride (9:1; v:v) for one hour. The device was rinsed extensively with chloroform and dried in air. The device was then immersed in a polymethylhydrosiloxane (PMHS) solution in toluene. The solution was refluxed for 24 hours with the addition of a few drops of $H_2PtCl_6$ in anhydrous THF at 2.5 hour intervals. The device was then washed with toluene and dried in air. To a toluene solution containing heptakis(2,3-O-dimethyl-6-O-8-octene-1-enyl)-b-cyclodextrin (example L) was immersed the above device. The solution was refluxed for 24 hours with the addition of $H_2PtC_6$ in anhydrous THF at 2.5 hour interval. The SAW device was rinsed with toluene and dried in air. The same films were fabricated similarly on a silicon wafer for characterization purposes. The final film has the following IR characteristics: C—H vibrations: 2856 $cm^{-1}$, 2879 $cm^{-1}$, 2925 $cm^{-1}$ and 2968 $cm^{-1}$.

Although the present invention has been described with reference to specific details, it is not intended that such details should be regarded as limitations upon the scope of the invention, except as and to the extent that they are included in the accompanying claims.

What is claimed is:

1. A method of detecting trace amounts of nitro-containing organic species or chemical warfare agents within an environment comprising:

placing a selected chemical sensor into an environment, said sensor including a substrate having an oxide surface layer thereon and a selective thin film of a cyclodextrin derivative chemically bound upon the substrate, said film adapted for the chemically bonding of a nitro-containing organic species or a chemical warfare agent therewith, for a sufficient time wherein nitro-containing organic species or chemical warfare agents can form complexes with said cyclodextrin derivative;

measuring a change resulting from complexation of nitro-containing organic species or chemical warfare agents with said cyclodextrin derivative;

correlating said measured change with a quantitative or qualitative output relating to said nitro-containing organic species or chemical warfare agents.

2. The method of claim 1 wherein said change is a weight change and measurement is by a surface acoustic wave device or lamb wave device including said selective thin film of a cyclodextrin derivative chemically bound upon a piezoelectric substrate of said device.

3. The method of claim 1 wherein said change is an index of refraction change and measurement is by an interferometer device including said selective thin film of a cyclodextrin derivative chemically bound upon an optical surface of said device.

4. The method of claim 1 wherein said detection is effective at detection limits of parts per billion.

5. The method of claim 2 wherein said detection is effective at detection limits of parts per billion.

6. The method of claim 3 wherein said detection is effective at detection limits of parts per billion.

7. A chemical microsensor comprising:

a substrate including an oxide layer;

a linking agent including a linear alkane chain containing from about 12 to about 18 carbon atoms attached to said oxide layer; and, a cyclodextrin-derivative covalently bonded to said linking agent.

8. The chemical microsensor of claim 7 wherein said cyclodextrin-derivative is covalently bonded to said linking agent through a urethane linkage.

9. A chemical microsensor system comprising:
- a first sensing portion including a first substrate having a surface oxide layer thereon;
- a linking agent including a linear alkane chain containing from about 8 to about 18 carbon atoms attached to said surface oxide layer of said first substrate;
- a cyclodextrin-derivative covalently bonded to said linking agent of first substrate;
- a second sensing portion including a second substrate having a surface oxide layer thereon;
- said linking agent including a linear alkane chain containing from about 8 to about 18 carbon atoms attached to said surface oxide layer of said second substrate, said first and second sensing portions electronically linked so as to provide measurements of a system wherein said second sensing portion serves as a reference to said first sensing portion.

* * * * *